(12) United States Patent
Iki et al.

(10) Patent No.: US 9,370,397 B2
(45) Date of Patent: *Jun. 21, 2016

(54) CARTILAGE TREATMENT PROBE

(71) Applicants: Kobi Iki, San Carlos, CA (US); William M. Ambrisco, Mountain View, CA (US); Douglas M. Lorang, Ripon, CA (US); Alan P. Gannon, Amesbury, MA (US); Richard M. Ranalli, Berwick, ME (US); Mathew E. Mitchell, Pelham, NH (US); Mark Markel, Middleton, WI (US); Ryland B. Edwards, III, Middleton, WI (US)

(72) Inventors: Kobi Iki, San Carlos, CA (US); William M. Ambrisco, Mountain View, CA (US); Douglas M. Lorang, Ripon, CA (US); Alan P. Gannon, Amesbury, MA (US); Richard M. Ranalli, Berwick, ME (US); Mathew E. Mitchell, Pelham, NH (US); Mark Markel, Middleton, WI (US); Ryland B. Edwards, III, Middleton, WI (US)

(73) Assignee: Smith & Nephew, Inc., Memphis, TN (US)

(*) Notice: Subject to any disclaimer, the term of this patent is extended or adjusted under 35 U.S.C. 154(b) by 230 days.

This patent is subject to a terminal disclaimer.

(21) Appl. No.: 13/933,341

(22) Filed: Jul. 2, 2013

(65) Prior Publication Data

US 2014/0018787 A1 Jan. 16, 2014

Related U.S. Application Data

(60) Continuation of application No. 13/616,504, filed on Sep. 14, 2012, now Pat. No. 8,500,734, which is a continuation of application No. 13/117,800, filed on May 27, 2011, now Pat. No. 8,377,058, which is a division of application No. 10/766,894, filed on Jan. 30, 2004, now Pat. No. 7,951,142.

(60) Provisional application No. 60/443,840, filed on Jan. 31, 2003.

(51) Int. Cl.
*A61B 18/14* (2006.01)
*A61B 18/18* (2006.01)

(52) U.S. Cl.
CPC .............. *A61B 18/18* (2013.01); *A61B 18/1402* (2013.01)

(58) Field of Classification Search
CPC .............. A61B 18/14; A61B 18/1402; A61B 18/00577; A61B 18/04; A61B 2018/00577; A61B 2018/00565; A61B 2018/00595; A61B 2018/1497
See application file for complete search history.

(56) References Cited

U.S. PATENT DOCUMENTS

| 5,895,386 | A | * | 4/1999 | Odell et al. ...................... 606/50 |
| 6,068,628 | A | * | 5/2000 | Fanton ............ A61B 17/320016 606/28 |
| 6,238,391 | B1 | * | 5/2001 | Olsen ................. A61B 18/1206 604/114 |
| 2001/0023347 | A1 | * | 9/2001 | Sharkey ............... A61B 18/148 606/41 |
| 2002/0107516 | A1 | * | 8/2002 | Sharkey ............... A61B 18/148 606/49 |
| 2003/0083652 | A1 | * | 5/2003 | Markel ................ A61B 18/148 606/41 |

* cited by examiner

*Primary Examiner* — Michael Peffley (57) ABSTRACT

An electrosurgical instrument for ablating cartilage while limiting collateral damage includes a non-conducting head with a small electrically conductive surface. The head of the instrument is coupled to a shaft by a flexible portion. The flexible portion biases the electrically conductive surface towards a tissue surface. The head is pivotably coupled to the shaft such that the electrically conductive surface is oriented substantially parallel to the tissue surface as the head slides across the tissue surface. A method of performing electrosurgery includes positioning the electrically conductive surface adjacent to the tissue surface, and sliding the shaft across the tissue surface with the head pivoting such that the electrically conductive surface is oriented substantially parallel to the tissue surface.

19 Claims, 9 Drawing Sheets

CARTILAGE TREATMENT PROBE

CROSS-REFERENCE TO RELATED APPLICATIONS

This application is a continuation of U.S. patent application Ser. No. 13/616,504, filed Sep. 14, 2012, titled "Cartilage Treatment Probe," now U.S. Pat. No. 8,500,734 which is a continuation of U.S. patent application Ser. No. 13/117,800, filed May 27, 2011, titled "Cartilage Treatment Probe,", U.S. Pat. No. 8,377,058 which is a divisional of U.S. patent application Ser. No. 10/766,894, filed Jan. 30, 2004, titled "Cartilage Treatment Probe," now U.S. Pat. No. 7,951,142, which claims priority under 35 U.S.C. §119(e) to U.S. Provisional Patent Application Ser. No. 60/443,840, filed on Jan. 31, 2003, titled "Cartilage Treatment Probe." The contents of the prior applications are hereby incorporated by reference in their entirety.

TECHNICAL FIELD

This disclosure relates generally to a probe for treating cartilage.

BACKGROUND

Articular cartilage is prone to diseases, such as chondromalacia and osteoarthritis, which result in fibrillation, or fraying, of the cartilage. Damaged cartilage is not as effective in maintaining stiffness and resilience, and in minimizing stress due to load. The diseases tend to degenerate over time if left untreated, and can result in the total loss of articular cartilage in the joint. It is desirable to treat these diseases to re-establish a smooth, stable articular surface.

SUMMARY

Radio-frequency energy delivered through a low-mass or low-surface area electrode can be used to rapidly debride cartilage fibrillations and smooth and/or seal the cartilage surface while producing minimal collateral damage, which typically occurs in the form of chondrocyte death and/or the excess removal of healthy tissue. Chondrocytes are the cells that maintain cartilage viability and growth. These cells are killed when exposed to temperatures of 45° C. or more. After death, chondrocytes tend not to regenerate.

The probe may include one or more of the following features. A non-conducting bumper that limits removal of excess amounts of cartilage; a flexible tip that facilitates optimum articular surface contact by the electrode over complex geometries, providing good accessibility to the tissue site of interest and safe operation; and software controls are designed such that the device operates in the ablative mode and effects of poor technique or misuse are minimized. The probe preferably operates in an ablative mode, with most of the RF energy involved in debriding and smoothing and little excess energy available to heat collateral tissue and cause excessive chondrocyte death.

The probe includes, e.g., a shaft and an electrically conductive surface. In embodiments, the electrically conductive surface is pivotably coupled, directly or indirectly, to the shaft, and is on a head or bumper at a distal portion of the shaft. The instrument can include a flexible portion, which is part of, or attached to, the shaft.

According to an aspect of the invention, an electrosurgical instrument includes a shaft, a flexible portion, and a head coupled to the shaft through the flexible portion. The head also is pivotably coupled to the flexible portion. The head includes an electrically conductive surface and the flexible portion is configured to bias the electrically conductive surface towards a tissue surface.

Embodiments of this aspect may include one or more of the following features.

The flexible portion includes a nitinol wire, a nitinol tube, a spring, or a distal portion of the shaft. The distal portion is corrugated, or has a radial cross section similar to a radial cross section of the remainder of the shaft. The flexible portion is configured to flex in at least one direction and the head is configured to pivot about an axis substantially perpendicular to that direction. The head also is configured to pivot in three dimensions about the flexible portion, wherein the head and the flexible portion are coupled by a ball-and-socket joint.

The head includes a slot about which the head is configured to pivot. The slot is a transverse slot pivotably receiving the flexible portion or pivotably receiving a wire, which may be rigid, coupled to the flexible portion. Alternatively, a living hinge is disposed between the head and the flexible portion. The living hinge is adjacent to and connects the head and the flexible portion, and the living hinge includes a section that is thinner than portions of the head and the flexible portion that are adjacent to the living hinge.

The head includes a non-conductive surface arranged relative to the electrically conductive surface to limit penetration of the electrically conductive surface into the tissue surface. The non-conductive surface is substantially planar. The electrically conductive surface projects from the non-conductive surface or is substantially flush with the non-conductive surface. The electrically conductive surface has a smaller surface area than the non-conductive surface.

The head includes an electrode that includes the electrically conductive surface. The electrode has a T-shape or an L-shape. The instrument further includes a return electrode, wherein the electrically conductive surface and the return electrode are configured to be coupled to opposite poles of an electrosurgical generator.

In illustrated embodiments, the head includes a first portion and a second portion. The first portion includes a projection and the second portion defines a hole that receives the projection. The projection is deformed to secure the projection in the hole. The first portion includes a groove and the second portion includes a ridge aligned with the groove. In a particular embodiment, the head has a substantially parallelepiped shape.

In another particular embodiment, the instrument further includes a sheath coupled to the shaft and moveable to at least partially cover the flexible portion and the head.

According to another aspect, a method of performing electrosurgery includes positioning an electrically conductive surface of a head of an instrument adjacent to a tissue surface. The head is pivotable relative to a shaft of the instrument. The method includes moving the shaft relative to the tissue surface with the head pivoting such that the electrically conductive surface is oriented substantially parallel to the tissue surface. The method may include biasing the electrically conductive surface towards the tissue surface using a flexible portion of the instrument.

According to another aspect, an electrosurgical instrument includes a shaft and a head that is coupled to the shaft. The head includes an electrically conductive surface. The head is pivotable relative to the shaft such that the electrically conductive surface is oriented substantially parallel to the tissue surface as the head moves across the tissue surface.

According to another aspect, an electrosurgical instrument includes a shaft and a head that is coupled to the shaft and pivotable relative to the shaft. The head includes an electrically conductive portion, for treating tissue, positioned at only one side of the head.

According to another aspect, an electrosurgical instrument includes a shaft and a head that is coupled to the shaft and that includes an electrically conductive surface. The head is configured to pivot relative to the shaft and to slide across a tissue surface as the electrically conductive surface is moved across the tissue surface.

According to another aspect, a method of performing electrosurgery includes positioning an electrically conductive surface of a head of an instrument adjacent to a tissue surface. The head is pivotably coupled to a shaft. The method includes sliding the head across the tissue surface. The head pivots relative to the shaft to facilitate the sliding.

According to another aspect, a method of treating chondromalacia includes positioning an electrically conductive surface of a head of an instrument adjacent to a cartilage surface. The head is pivotable relative to a shaft of the instrument. The method includes moving the shaft relative to the cartilage surface. The head pivots relative to the cartilage surface. The method includes applying electrical energy to the electrically conductive surface to treat chondromalacia.

According to another aspect, an electrosurgical instrument includes a shaft, a resiliently flexible portion, and a head. The head is pivotably coupled to the resiliently flexible portion and the head is coupled to the shaft through the resiliently flexible portion. The head includes a substantially planar tissue contact surface including an electrically conductive portion.

Embodiments of this aspect may include one or more of the following features. The shaft defines a longitudinal axis and the head is offset from the axis. The resiliently flexible portion includes a distal portion of the shaft. The substantially planar contact surface includes a non-conductive portion. The non-conductive portion has a larger surface area than the electrically conductive portion. An electrical lead is coupled to the electrically conductive portion.

According to another aspect, an electrosurgical instrument includes a conducting mean for applying energy to a region of tissue. The instrument includes a flexing means coupled to the conducting means for biasing the conducting means towards the region of tissue. The instrument includes a pivoting means for pivoting the conducting means relative to the flexing means.

According to another aspect, an electrosurgical instrument includes a shaft, a conducting means for applying energy to a tissue surface, and a pivoting means for pivoting the conducting means relative to the shaft.

Embodiments of this aspect may include one or more of the following features.

The electrosurgical instrument includes flexing means coupled to the conducting means for biasing the conducting means towards the tissue surface. The flexing means includes a flexible portion. The flexible portion is configured to bias the conductive surface towards the tissue surface. The conducting means includes an electrically conductive surface. The pivoting means includes a head pivotably coupled to the flexing means, and the head includes the electrically conductive surface.

The electrosurgical instrument includes a resiliently flexible portion. The conducting means includes an electrically conductive surface. The pivoting means includes a head coupled to the shaft through the resiliently flexible portion and pivotably coupled to the resiliently flexible portion. The head includes a substantially planar tissue contact surface including the electrically conductive portion.

The conducting means includes an electrically conductive surface. The pivoting means includes a head coupled to the shaft and including the electrically conductive surface. The head is pivotable relative to the shaft such that the electrically conductive surface is oriented substantially parallel to the tissue surface as the head moves across the tissue surface.

The pivoting means includes a head that is coupled to the shaft and that is pivotable relative to the shaft. The conducting means includes an electrically conductive surface included on, and positioned at only one side of, the head.

The conducting means includes an electrically conductive surface. The pivoting means includes a head coupled to the shaft and including the electrically conductive surface. The head is configured to pivot relative to the shaft and to slide across the tissue surface as the electrically conductive surface is moved across the tissue surface.

According to another aspect, a method of performing electrosurgery includes positioning an electrically conductive surface of a head of an instrument adjacent to a tissue surface. The head is pivotable relative to a shaft of the instrument.

Embodiments of this aspect may include one or more of the following features. The method includes moving the shaft relative to the tissue surface with the head pivoting such that the electrically conductive surface is oriented substantially parallel to the tissue surface. The method includes sliding the head across the tissue surface. The head pivots relative to the shaft to facilitate the sliding. The method includes moving the shaft relative to a cartilage surface of the tissue surface. The head pivots relative to the cartilage surface. The method further includes applying electrical energy to the electrically conductive surface to treat chondromalacia.

The details of one or more embodiments are set forth in the accompanying drawings and the description below. Other features will be apparent from the description and drawings, and from the claims.

DETAILED DESCRIPTION

Figure 1:
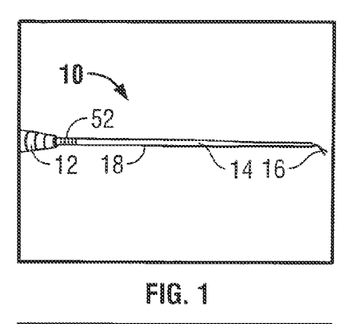
FIG. 1 is a side view of an embodiment of a cartilage treatment probe.

Referring to FIG. 1, a cartilage treatment probe 10 includes a proximal section 12 for attachment to a radiofrequency power supply, a shaft 14, and a distal, active tip 16. Shaft 14 is formed from a stainless steel tube 17 (see FIG. 3) covered with insulation, e.g., heat shrink tubing, which is surrounded by a sheath 18.

Figure 2:
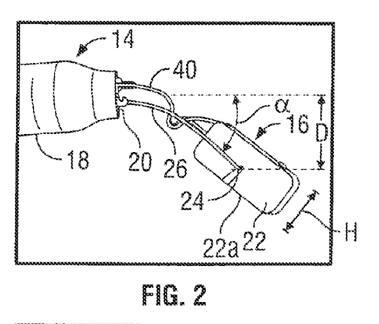
FIG. 2 is a side view of an active tip of the probe shown in FIG. 1.
Figure 3:
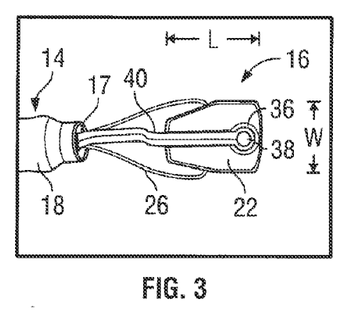
FIG. 3 is a top view of the tip shown in FIG. 1.

Referring to FIGS. 2 and 3, tip 16 extends from a distal end 20 of shaft 14. Tip 16 includes a bumper, or head, 22 formed from one or more electrically insulating materials, e.g., an electrically insulating ceramic or tetrafluoroethylene (TFE) material, that has a generally planar tissue contacting surface 22a. Bumper 22 defines a transverse slot 24 for pivotably coupling bumper 22 to a flexible portion, i.e., a nitinol wire form 26.

Figure 4:
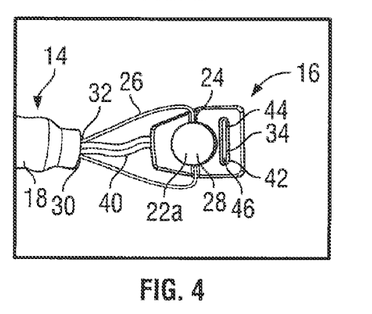
FIG. 4 is a bottom view of the tip shown in FIG. 1.

As shown in FIG. 4, nitinol wire form 26 loosely resides in transverse slot 24. Wire form 26 is in a super-elastic state, as explained below. Wire form 26 is held in place by a retainer disk 28 that is glued to bumper 22 or snaps into bumper 22, allowing bumper 22 to pivot freely about nitinol wire form 26. The proximal ends 30, 32 of wire form 26 are attached to distal end 20 of shaft 14, such as by being inserted into distal end 20 of shaft 14 and crimped to stainless steel tube 17. Bumper 22 pivots about an axis defined by wire form 26 that is substantially perpendicular to the longitudinal axis of shaft 14, although this orientation can be varied. Nitinol wire form 26 is arranged so that, in a relaxed state, bumper 22 is offset from a longitudinal axis of shaft 14 by a distance D and by an angle α, as shown in FIG. 2, to facilitate accessing tissue with bumper 22.

Referring again to FIG. 2, bumper 22 has a height H in the range of about 0.05 to 0.15 inches, preferably about 0.09 inches, a width W in the range of about 0.10 to 0.19 inches, preferably about 0.14 inches, and a length L in the range of about 0.10 to 0.30 inches, preferably about 0.20 inches. Bumper 22 is offset from the longitudinal axis of shaft 14 distance D in the range of about 0.01 to 0.40 inches, preferably about 0.15 inches. The distance D is measured from the longitudinal axis of shaft 14 to a line parallel to the longitudinal axis that intersects transverse slot 24, as shown in FIG. 2. The angle α is approximately 30 degrees. Angle α can range from about 0 to 45 at least about degrees on either side of the longitudinal axis.

Referring again to FIGS. 3 and 4, tip 16 includes a "T" shaped electrode 34 having a stem 38 and a top 44. Electrode 34 is made from an electrically conductive material, e.g., stainless steel flat stock or a wire form. Bumper 22 defines a hole 36 and stem 38 of the "T" is located in hole 36. Soldered, or otherwise attached, to the end of stem 38 is a power lead 40. Power lead 40 is a thin flexible conductor strip chosen for its flexibility and low profile. Proximal of tip 16, power lead 40 is positioned between tube 17 and the heat shrink tubing surrounding tube 17, and extends to the proximal end of probe 10 for connection to a cable running to the power supply. Bumper 22 also defines a cut-out 42 in tissue contacting surface 22a, in which top 44 of the "T" resides to form an electrically conductive, active portion 46 of the electrode, for applying energy to tissue. Top 44, which forms an electrically conductive surface of portion 46, is substantially planar but other surface geometries can be used.

Figure 5:
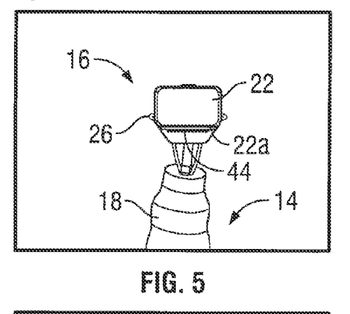
FIG. 5 is an end view of the tip shown in FIG. 1.

Referring to FIG. 5, top 44 of the "T" is positioned in bumper 22 such that electrically conductive portion 46 is flush with tissue contacting surface 22a or extends out from tissue contacting surface 22a by about 0.0003 to 0.004 inches. Portion 46 also can be recessed in tissue contacting surface 22a by about 0.0003 to 0.004 inches. The active, electrically conductive portion 46 of the electrode preferably has a small surface area in the range of about 0.0002 to 0.0065 square inches, preferably about 0.0009 to 0.0036 square inches, more preferably in the range of about 0.0016 to 0.0021 square inches, and most preferably about 0.0018 square inches. The surface area of portion 46 is substantially smaller than the surface area of tissue contacting surface 22a, which can be, for example, in the range of about 0.01 to 0.057 square inches, preferably about 0.028 square inches. Bumper 22 acts as a physical barrier to limit the depth of penetration of electrode 34 into the tissue. Bumper 22 also masks portions of electrode 34, except for portion 46, to limit the direction of current flow from electrode 34. Power lead 40 and stem 38 of electrode 34 are surrounded by an insulating material (not shown) such that portion 46 is exposed only on tissue contacting surface 22a of bumper 22.

Figure 6:
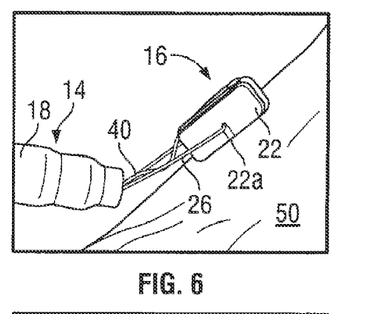
FIGS. 6 and 7 show the tip of the probe shown in FIG. 1 positioned on an articular surface.
Figure 7:
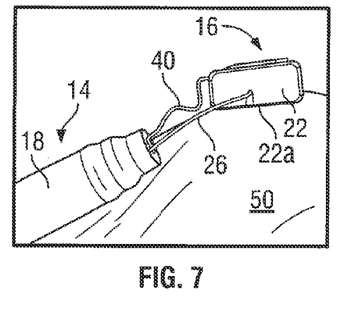

Referring to FIGS. 6 and 7, in use, probe 10 can be positioned adjacent to a tissue surface 50 to be treated, so that the electrically conductive surface of portion 46 is substantially parallel to tissue surface 50. Radio frequency power is delivered to portion 46 from a radio frequency generator (not shown), such as, for example, the Vulcan® generator sold by Smith & Nephew, Inc, Andover, Mass. As probe 10 is moved across tissue surface 50, bumper 22 pivots freely about nitinol wire form 26 to facilitate tissue contacting surface 22a sliding across tissue surface 50 and the surface of electrically conductive portion 46 remaining substantially parallel to tissue surface 50. Nitinol wire form 26, which is extremely flexible in multiple directions, provides tip 16 with a range of flexibility relative to shaft 14 such that bumper 22 and the active, electrically conductive portion 46 of electrode 34 remains substantially in contact with articular tissue surface 50 while traveling over complex geometries. The resistance to deformation of the nitinol in its superelastic state is constant, providing a spring action that helps bumper 22 and the electrically conductive surface of portion 46 follow the curvature of tissue surface 50 while maintaining a controlled, approximately uniform contact pressure of the bumper 22 and electrode 34 against articular cartilage surface 50 over complex geometries as nitinol wire 26 is deflected. The spring action of nitinol wire 26 also biases bumper 22 towards tissue surface 50 when probe 10 is pressed towards tissue surface 50. Nitinol wire 26 can be referred to as a spring, and other springs or spring materials, such as, for example, stainless steel spring wire, can be used.

Figure 8:
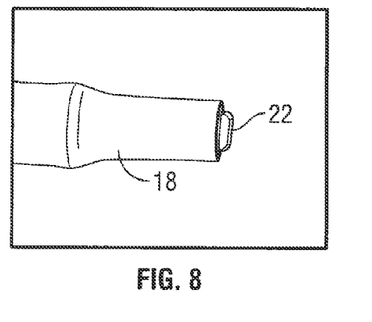
FIG. 8 shows the tip of the probe shown in FIG. 1 with an outer sheath of the probe advanced over the tip.

Referring to FIG. 8, sheath 18 can be slid forward relative to stainless steel tube 17 to cover tip 16 to provide temporary rigidity to flexible tip 16 for insertion into and removal from the joint capsule. Sheath 18 includes ribs 52 (FIG. 1) that facilitate grasping of sheath 18 to extend and retract sheath 18. When covering tip 16, sheath 18 also protects tip 16 and limits catching of tip 16 on tissue.

Power is preferably delivered to probe 10 under the control of an impedance feedback loop to maintain the probe in an ablative mode. In addition, since the impedance rises when the probe is not being moved across tissue, impedance feedback can be used to recognize when the probe is not being moved and controls can be used to turn off the power and/or sound an alarm. Probe 10 also can include one or more temperature sensors, such as a thermistor mounted in tip 16, to monitor the temperature at or near tip 16. The temperature sensors and the power generator can be coupled by a feedback control system that regulates the amount of energy delivered to the probe based on the temperature at or near tip 16, in order to control the temperature of tissue surface 50. These control systems can be implemented, for example, in software.

The use of a small surface area electrode allows the probe to function in an ablative mode at low power and provides for low thermal penetration into the tissue such that the extent of cell death can be maintained at preferably less than about 200 microns. This results in surface smoothing of the cartilage of the articular surface with minimal tissue removal and cell death. The use of probe 10 is indicated, e.g., for chondromalacia lesions Outerbridge System Grades II and III, as well as for stabilizing the rim of Grade IV lesions. It is believed that an additional benefit of the use of probe 10 is the sealing of articular surfaces to stop or slow down the degradation process of the cartilage.

Probe 10 has been shown as a monopolar device. A monopolar device has certain advantages over a bipolar device, such as the smaller size of the monopolar device facilitating access to small joint spaces, and the presence of only one electrode in the joint space so the user does not have to be concerned with inadvertent contact of a return electrode with tissue. However, the probe can be bipolar by incorporating a return electrode on the shaft or elsewhere on the probe, as discussed with respect to FIG. 9 below.

Stainless steel tube 17 need not define a lumen along its entire length, but need only be able to receive ends 30 and 32 of the nitinol wire 26 to attach ends 30 and 32 to the distal end 20 of tube 17. For example, tube 17 can be solid along the majority of its length, providing additional rigidity to the probe, and include one or two openings at distal end 20 of tube 17 into which ends 30 and 32 of nitinol wire 26 are inserted.

Figure 9:
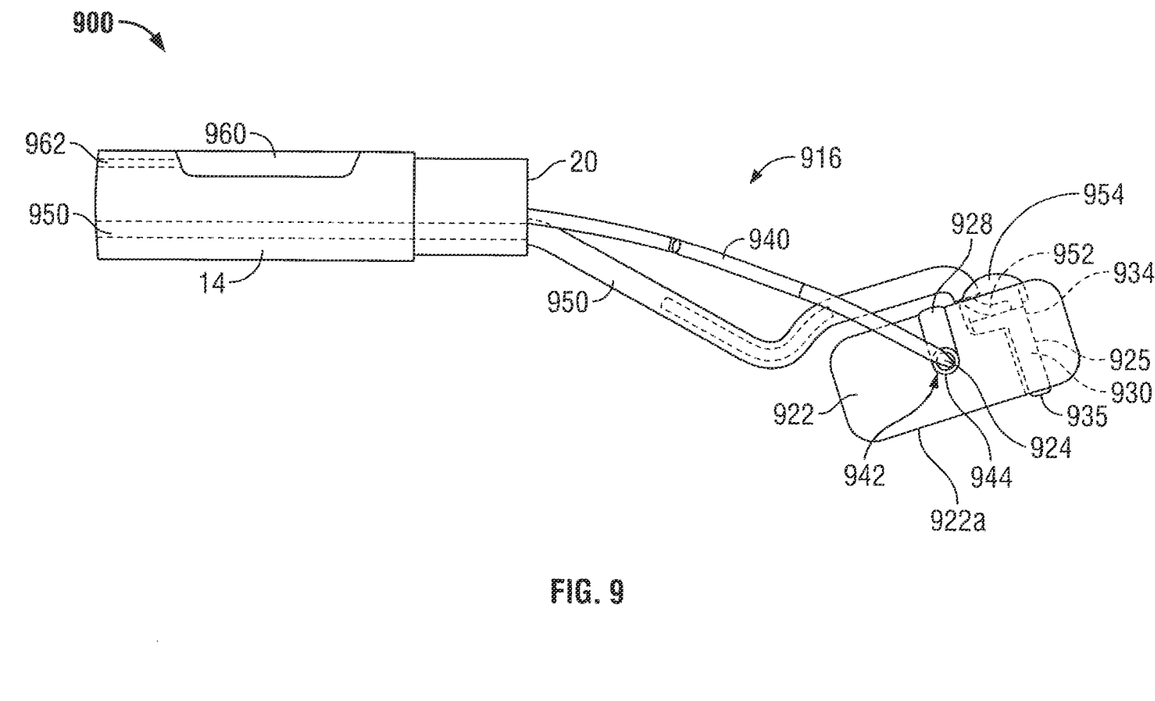
FIG. 9 is a side view of a second embodiment of a cartilage treatment probe.

Referring to FIG. 9, an alternate embodiment of a cartilage treatment probe 900 includes an active tip 916 that attaches to distal end 20 of shaft 14, as discussed above. Active tip 916 includes a bumper, or head, 922, having a tissue contacting surface 922a. Tissue contacting surface 922a includes an electrically conductive surface 935 of an active electrode 930 for applying energy to tissue. Electrically conductive surface 935 is rounded and extends out from tissue contacting surface 922a a small amount, such as approximately 0.0003 to 0.004 inches. Alternatively, electrically conductive surface 935 can be flush with or recessed in tissue contacting surface 922a. Electrically conductive surface 935 has a surface area substantially smaller than tissue contacting surface 922a, as discussed above.

Bumper 922 defines a transverse slot 924 that receives a nitinol wire 940, or more generally a flexible member, for pivotably coupling bumper 922 to shaft 14, as discussed above. A portion 942 of nitinol wire 940 is located in slot 924 and is surrounded by a sleeve 944 to facilitate pivoting of bumper 922 about nitinol wire 940. Slot 924 is closed off with a non-conductive filler material 928, which can be the same as or different from the material of bumper 922, in order to hold nitinol wire 940 in slot 924, while allowing bumper 922 to pivot about nitinol wire 940.

Active electrode 930 is L-shaped and bumper 922 defines a corresponding L-shaped aperture 925 for receiving active electrode 930. Also within L-shaped aperture 925, a distal portion 952 of an active power lead 950 is soldered, or otherwise attached, to a top surface 934 of active electrode 930. Distal portion 952 of active power lead 950 and top surface 934 of active electrode 930 are closed off by an electrically insulating filler 954, which is the same or a different material than bumper 922. Accordingly, active electrode 930 is exposed only at electrically conductive surface 935, and bumper 922 includes an electrically conductive portion for treating tissue positioned at only one side (tissue contacting surface 922a) of bumper 922. It should be understood that electrode 930 and aperture 925 can have any other suitable geometry that allows electrode 930 to be mounted to bumper 922.

Shaft 14 also includes an electrically conductive surface of a return electrode 960 coupled to a return power lead 962. Return electrode 960 is shown flush with the outer surface of shaft 14, but return electrode 960 can project from or be recessed in shaft 14. For example, shaft 14 can be formed by a stainless steel tube covered with insulation, and return electrode 960 can be disposed over the insulation. Another layer of insulation can be disposed over a portion of return electrode 960 and/or return power lead 962. Return electrode 960 and/or return power lead 962 also can be formed from the stainless steel tube.

Active power lead 950 and return power lead 962 are coupled to opposite poles of a bipolar electrosurgical generator (not shown), such as the aforementioned Vulcan® generator. Thus, probe 900 operates in a bipolar mode with current mainly flowing from electrically conductive surface 935, through or around the tissue surface, to return electrode 960. It should be understood that return electrode can be located on another part of probe 10, such as, for example, on bumper 22 or on nitinol wire 940.

Figure 10:
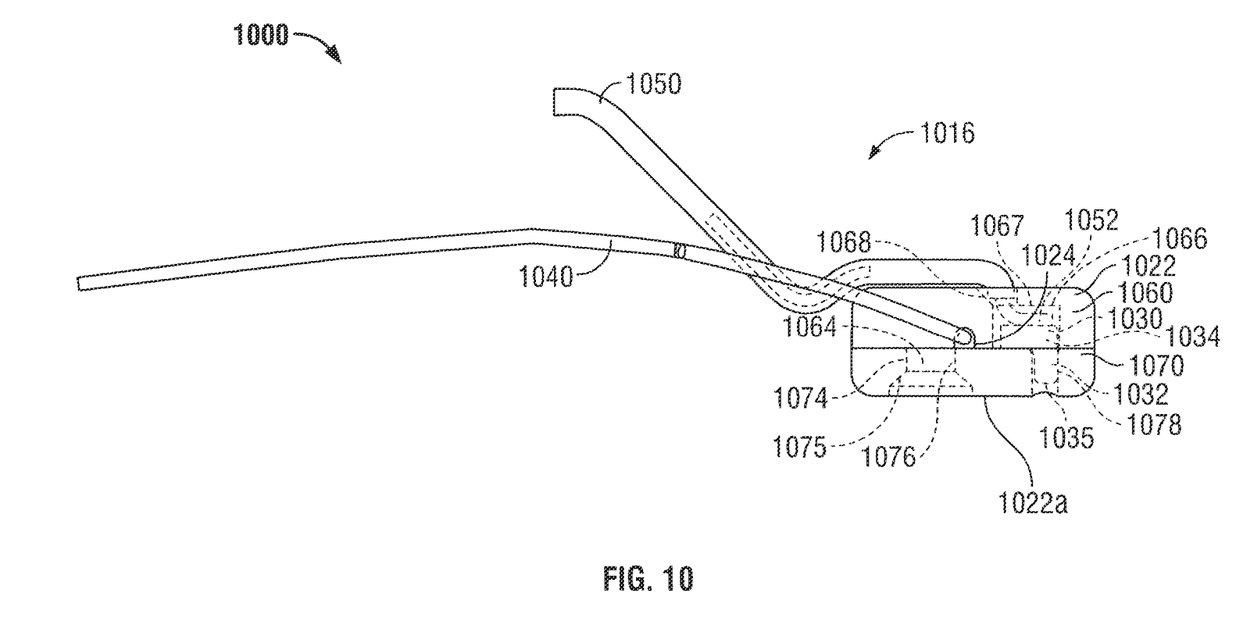
FIG. 10 is a side view of a third embodiment of a cartilage treatment probe.

Referring to FIG. 10, an alternative embodiment of a cartilage treatment probe 1000 includes an active tip 1016 that attaches to distal end 20 of shaft 14, as discussed above. Active tip 1016 includes a bumper, or head, 1022 having a tissue contacting surface 1022a. Tissue contacting surface 1022a of bumper 1022 includes an electrically conductive surface 1035 of an electrode 1030 for applying energy to tissue. Electrically conductive surface 1035 is rounded and is recessed within tissue contacting surface 1022a a small amount, such as approximately 0.0003 to 0.004 inches. Alternatively, electrically conductive surface 1035 can be flush with or extend from tissue contacting surface 1022a, as discussed above. Electrically conductive surface 1035 also has a surface area substantially smaller than a surface area of tissue contacting surface 1022a, as discussed above.

Figure 11:
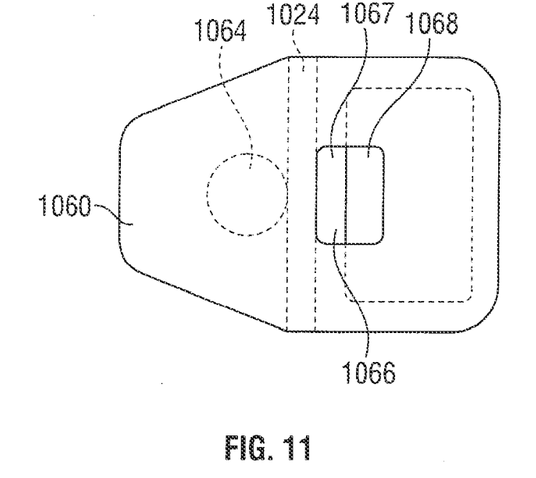
FIG. 11 is a top view of an upper bumper portion of the cartilage treatment probe of FIG. 10.
Figure 14:
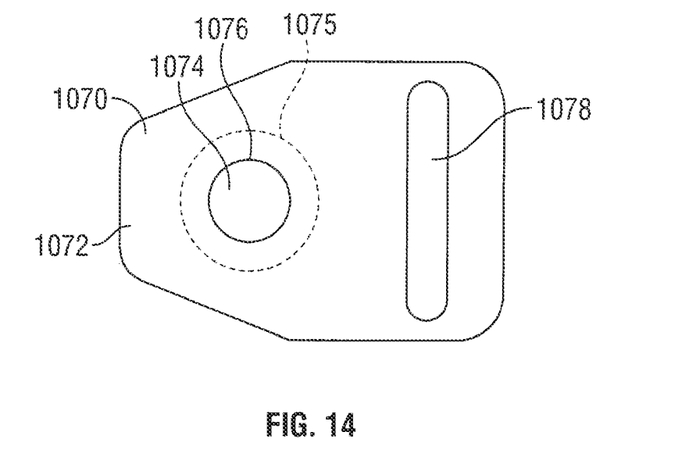
FIG. 14 is a top view of a lower bumper portion of the cartilage treatment probe of FIG. 10.
Figure 15:
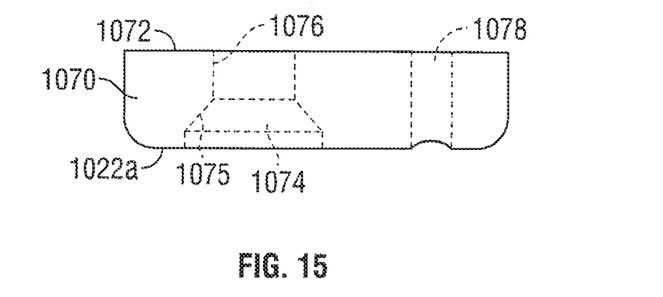
FIG. 15 is a side view of the lower bumper portion of the cartilage treatment probe of FIG. 10.
Figure 16:
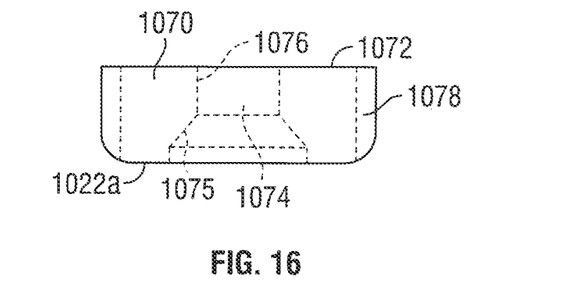
FIG. 16 is a front end view of the lower bumper portion of the cartilage treatment probe of FIG. 10.

Bumper 1022 defines a transverse slot 1024 that receives a flexible portion 1040, which is a nitinol wire, for pivotably coupling bumper 1022 to shaft 14, as discussed above. Bumper 1022 includes an upper bumper portion 1060 (FIGS. 11-13) and a lower bumper portion 1070 (FIGS. 14-16). Upper bumper portion 1060 and lower bumper portion 1070 are made of the same or different non-conductive materials, such as ceramic or TFE.

Figure 12:
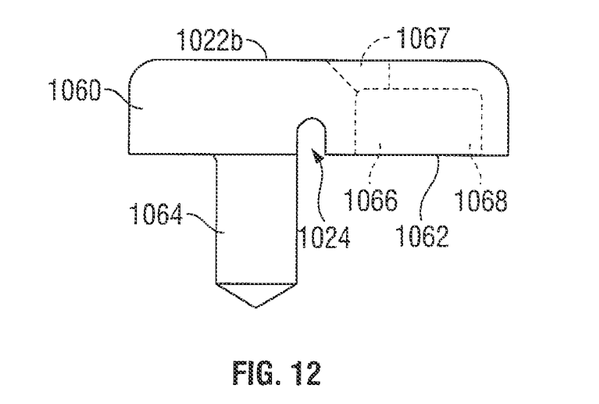
FIG. 12 is a side view of the upper bumper portion of the cartilage treatment probe of FIG. 10.
Figure 13:
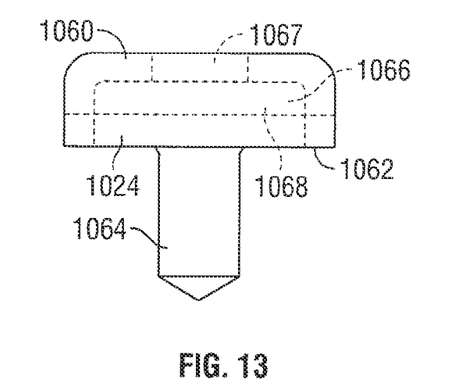
FIG. 13 is a front end view of the upper bumper portion of the cartilage treatment probe of FIG. 10.

Referring to FIGS. 10-13, upper bumper portion 1060 includes transverse slot 1024, an upper mating surface 1062, and a cylindrical projection 1064 projecting down from upper mating surface 1062. Upper bumper portion 1060 also includes an upper electrode receiving aperture 1066 configured to receive a top portion 1034 of L-shaped electrode 1030 and an end portion 1052 of a power lead 1050. As shown in FIGS. 10 and 12, upper electrode receiving aperture 1066 includes a rectangular portion 1067 intersecting upper mating surface 1062 and a tapered portion 1068 intersecting an upper surface 1022b of bumper 1022.

Referring to FIGS. 10 and 14-16, lower bumper portion 1070 includes tissue contacting surface 1022a and a lower mating surface 1072. Lower bumper portion 1070 also includes a substantially round projection receiving hole 1074 for receiving projection 1064 of upper bumper portion 1060. Hole 1074 includes a tapered section 1075 that tapers from a larger diameter at a point near tissue contacting surface 1022*a* to a smaller diameter approximately halfway through hole 1074. Hole 1074 also includes a constant diameter section 1076 that extends from the point halfway through the hole 1076 to lower mating surface 1072 as discussed below. Lower bumper portion 1070 also includes a lower electrode receiving aperture 1078 for receiving a lower portion 1032 of L-shaped electrode 1030.

Bumper 1022 is assembled by passing nitinol wire 1040 through slot 1024, seating electrode 1030 as explained below, and aligning upper mating surface 1062 of upper portion 1060 and lower mating surface 1072 of lower portion 1070 such that projection 1064 passes through projection receiving hole 1074. L-shaped electrode 1030 is seated in electrode receiving apertures 1066 and 1078 such that bottom portion 1032 is seated in lower aperture 1078 and top portion 1034 is seated in rectangular portion 1067 of upper aperture 1066. Bottom portion 1032 of electrode 1030 is exposed at tissue contacting surface 1022*a* to form electrically conductive surface 1035. Projection 1064 is heated to deform projection 1064 so that projection 1064 fills tapered section 1075 of projection receiving hole 1074 and locks upper bumper portion 1060 to lower bumper portion 1070. In doing so, projection 1064 is made to be flush with tissue contacting surface 1022*a*.

End portion 1052 of power lead 1050 passes through tapered portion 1068 and into rectangular portion 1067 of upper aperture 1066 and is electrically connected to electrode 1030 to transmit electrical energy to electrode 1030. The portion of power lead 1050 outside of bumper 1022 is covered with an electrically insulating material. When assembled, only electrically conductive surface 1035 of electrode 1030 is exposed, on tissue contacting surface 1022*a* of bumper 1022. Power lead 1050 is coupled to an electrosurgical generator (not shown) for delivering monopolar energy to electrically conductive surface 1035.

Figure 17:
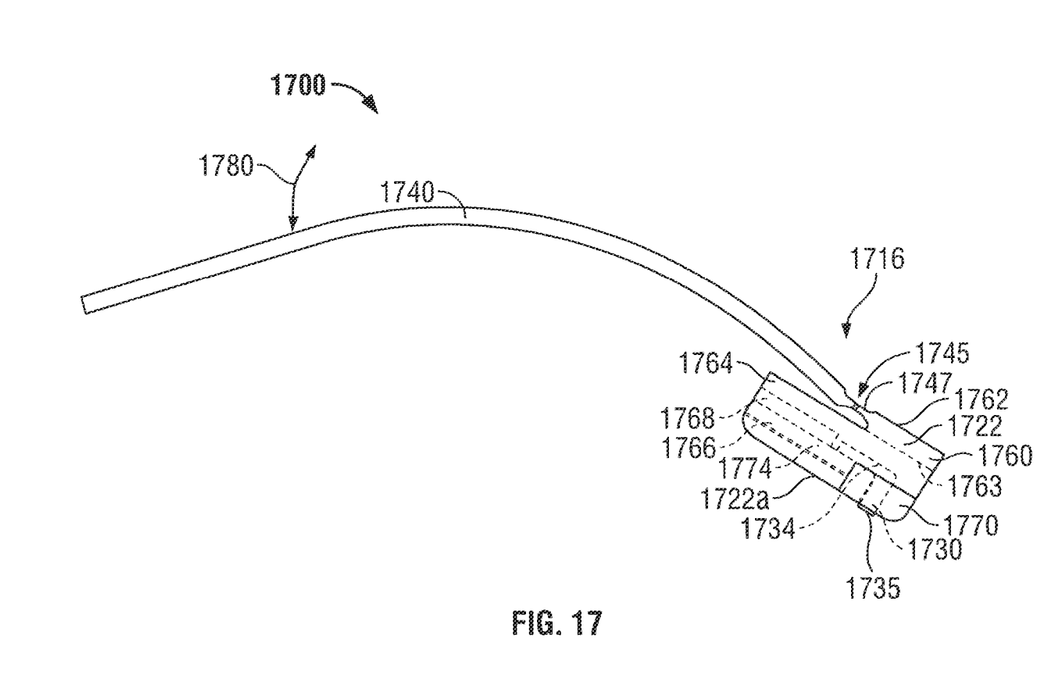
FIG. 17 is a side view of a fourth embodiment of a cartilage treatment probe.

Referring to FIG. 17, an alternative embodiment of a cartilage treatment probe 1700 includes an active tip 1716. Active tip 1716 includes a flexible portion 1740, a bumper, or head, 1722 and a living hinge 1745. Flexible portion 1740 is coupled to distal end 20 of shaft 14 (e.g., as shown in FIG. 1), such as by ultrasonic welding. Flexible portion 1740 is resiliently flexible, has a rectangular cross section, and is made of an elastic or superelastic material, such as plastic. Flexible portion 1740 biases bumper 1722, as discussed above.

Bumper 1722 has a tissue contacting surface 1722*a*, which includes an electrically conductive surface 1735 of an L-shaped electrode 1730 for applying energy to tissue. Electrically conductive surface 1735 is rounded, extends out from tissue contacting surface 1722*a* a small amount and has a surface area substantially smaller than a surface area of tissue contacting surface 1722*a*, as discussed above. Alternatively, electrically conductive surface 1735 can be flush with or recessed in tissue contacting surface 1722*a*, as discussed above. Electrode 1730 is exposed only at electrically conductive surface 1735 on tissue contacting surface 1722*a*.

Figure 18:
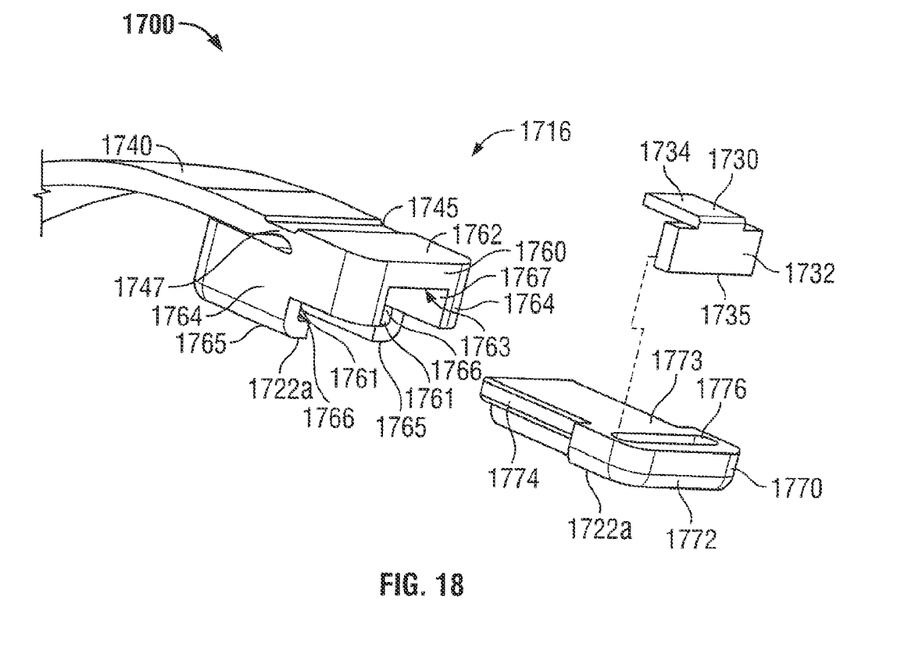
FIG. 18 is an exploded perspective view of the cartilage treatment probe of FIG. 17.

Referring to FIGS. 17 and 18, bumper 1722 includes a lower bumper portion 1770 and an upper bumper portion 1760. Lower bumper portion 1770 and upper bumper portion 1760 are made of the same or different non-conductive materials, such as ceramic or TFE. Lower bumper portion 1770 includes a portion of tissue contacting surface 1722*a*. Lower bumper portion 1770 is substantially T-shaped, including a distal portion 1772 and a proximal portion 1773. Projecting laterally from proximal portion 1773 are lateral ridges 1774 (only one of which is shown). Distal portion 1772 includes an electrode receiving aperture 1776 for receiving a bottom portion 1732 of L-shaped electrode 1730.

Upper bumper portion 1760 includes a top wall 1762 and lateral depending walls 1764 arranged in a U-shaped configuration when viewed from a distal end of bumper 1722. Each of lateral depending walls 1764 terminate has a terminal end 1765 that forms a portion of tissue contacting surface 1722*a*. An interior surface 1761 of each lateral depending wall 1764 defines a groove 1766 for receiving lateral ridges 1774 of lower bumper portion 1770. An interior surface 1763 of top wall 1762 and interior surfaces 1761 define a space 1767 for receiving a top portion 1734 of L-shaped electrode 1730.

Bumper 1722 is assembled by inserting bottom portion 1732 of L-shaped electrode 1730 into aperture 1776 in lower bumper portion 1770. Proximal portion 1773 of lower bumper portion 1770 is inserted into upper bumper portion 1760 so that lateral ridges 1774 are aligned with or fit into grooves 1766, and top portion 1734 of electrode 1730 is received in space 1767 defined by interior surfaces 1761 and 1763. Upper bumper portion 1760 and lower bumper portion 1770 are locked together by friction fit or by other means such as, for example, an adhesive. Assembled bumper 1722 defines a rear opening 1768 configured to receive a power lead (not shown) for attachment to electrode 1730. The remaining space between electrode 1734 and interior surfaces 1731, 1733 is filled with a non-conductive material, such as, for example, a ceramic or plastic epoxy.

Bumper 1722 is pivotably coupled to flexible portion 1740 by a living hinge 1745 disposed between flexible portion 1740 and bumper 1722. Living hinge 1745 includes a thin section 1747 of material integral with flexible portion 1740 and bumper 1722. Thin section 1747 has a thickness of approximately 0.006 inches, although other dimensions can be used. Flexible portion 1740, upper bumper portion 1760, and living hinge 1745 are, for example, molded from a single piece of material. Living hinge 1745 is composed of a flexible material, such as, for example, polypropylene or polyethylene, that can flex a large number of times without failure. Living hinge 1745 allows bumper 1722 to pivot relative to flexible portion 1740, about thin section 1747 as shown by arrow 1780.

Figure 19:
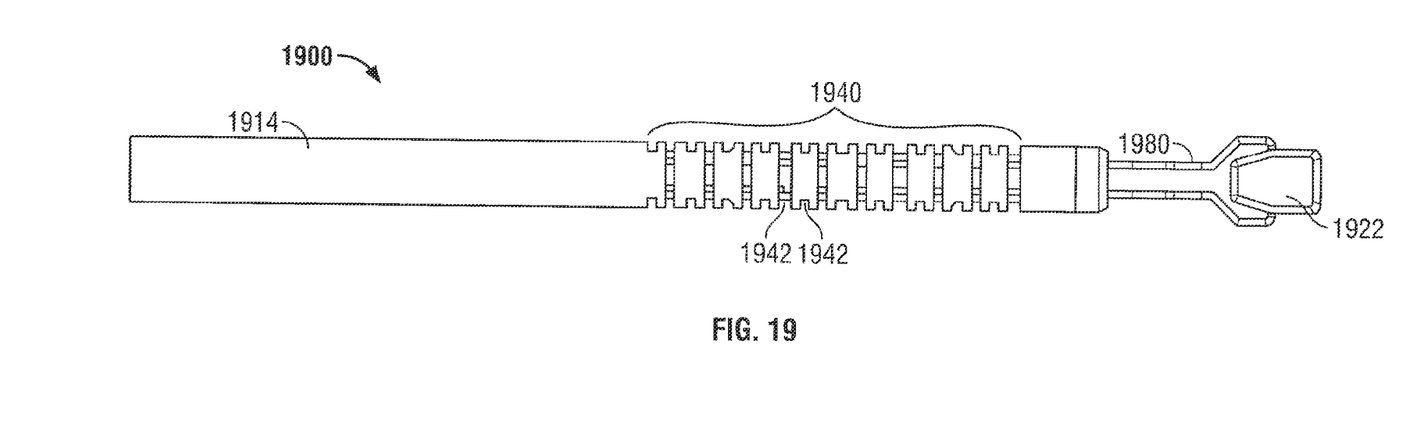
FIG. 19 is a side view of a fifth embodiment of a cartilage treatment probe.
Figure 20:
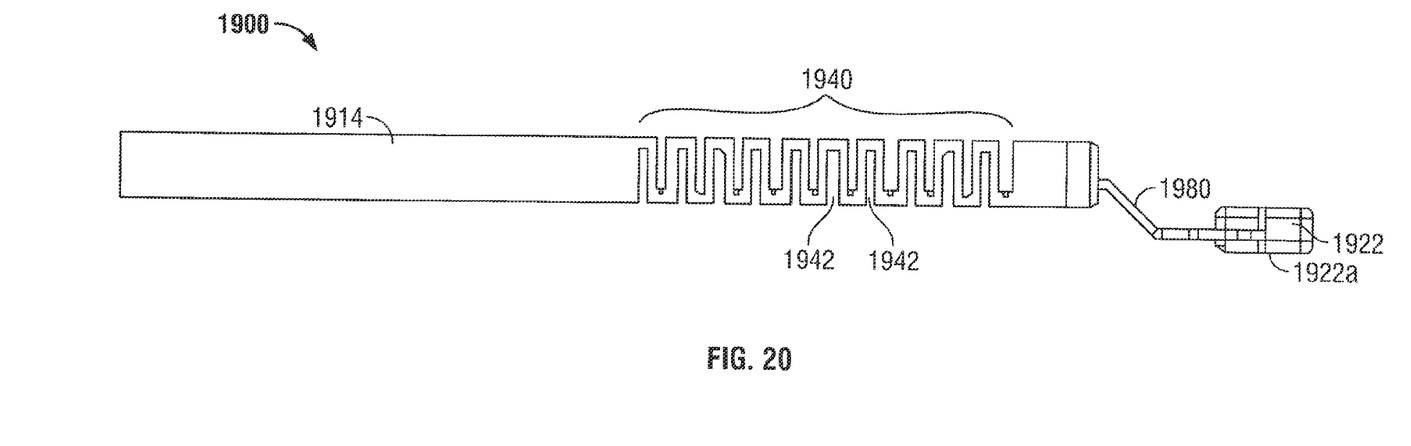
FIG. 20 is a top view of the cartilage treatment probe shown in FIG. 19.

Referring to FIGS. 19 and 20, an alternate embodiment of a cartilage treatment probe 1900 includes a shaft 1914, a wire 1980, and a bumper, or head, 1922. Bumper 1922 is indirectly pivotably coupled to a flexible distal portion 1940 of shaft 1914 by wire 1980. Rather than wire 1980 being resiliently flexible, wire 1980 is made from a rigid material, such as stainless steel or plastic, and flexibility is provided by flexible distal portion 1940 of shaft 1914. Flexible distal portion 1940 includes a plurality of cutouts 1942 to form a resiliently flexible, corrugated structure. At points between adjacent cutouts 1942, flexible distal portion 1940, has a radial (or transverse) cross-section that is circular and that is substantially similar to the radial cross-section of the remainder of shaft 1914 proximal of flexible portion 1940.

Bumper 1922 can be, for example, any of bumpers 22, 922, 1022, or 1722 and includes an electrode (not shown). Bumper 1922 is pivotably coupled to wire 1980, as discussed above. Wire 1980 is bent so that bumper 1922 is offset from a longitudinal axis of shaft 1914 a distance, as discussed above, to facilitate accessing a tissue surface with a tissue contacting surface 1922*a* of bumper 1922. Bumper 1922 is generally parallel to the longitudinal axis, but could be offset by an angle, as discussed above, such as by making flexible portion 1940 curved.

Figure 21:
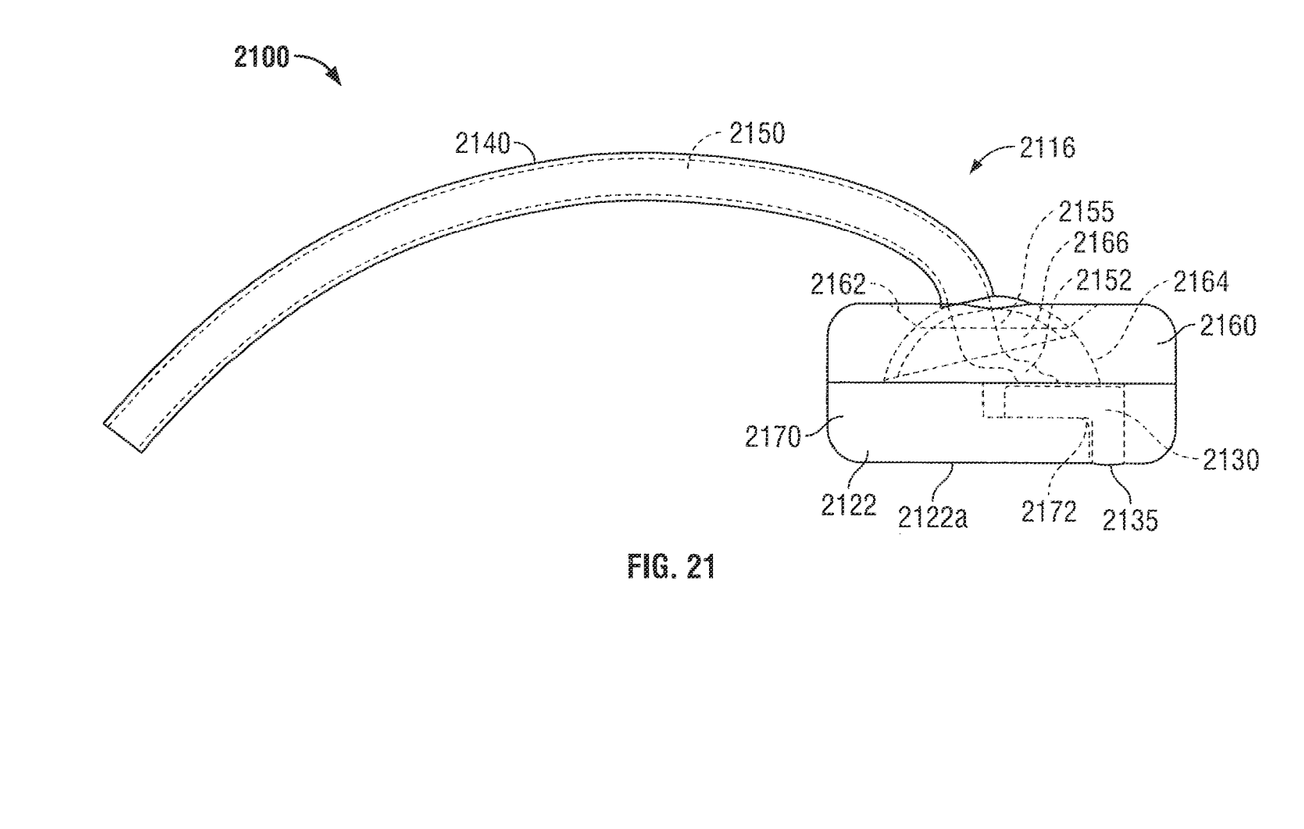
FIG. 21 is a side view of a sixth embodiment of a cartilage treatment probe.

Referring to FIG. 21, an alternative embodiment of a cartilage treatment probe 2100 includes an active tip 2116 having a bumper, or head, 2122, pivotably coupled to a resiliently flexible portion 2140. Bumper 2122 includes an upper bumper portion 2160 and a lower bumper portion 2170, each made of a non-conductive material, such as ceramic or plastic. Upper bumper portion 2160 and lower bumper portion 2170 are joined to one another, for example, by applying an adhesive, brazing, or ultrasonic welding, or by one of the other mechanisms discussed above. Flexible portion 2140 is coupled to shaft 14, as discussed above.

Lower bumper portion 2170 includes a tissue contacting surface 2122a and an L-shaped recess 2172 for receiving an L-shaped electrode 2130, as discussed above. L-shaped electrode 2130 includes an electrically conductive surface 2135 that is flush with tissue contacting surface 2122a. Alternatively, an electrically conductive surface 2135a projects from tissue contacting surface 2122a or an electrically conductive surface 2135b is recessed in tissue contacting surface 2122a. Electrically conductive surface 2135 has a surface area substantially smaller than tissue contacting surface 2122a.

Upper bumper portion 2160 defines a recess 2162 and a cavity 2164 that receives, in mating relationship, a substantially dome-shaped member 2166. Member 2166 is fixedly attached to a distal end of flexible member 2140, which is, for example, a nitinol tube. Member 2166 and cavity 2164 function like a ball-and-socket joint, allowing bumper 2122 to pivot in three dimensions about dome shaped member 2166 and flexible member 2140. The three-dimensional pivoting facilitates the sliding of tissue contacting surface 2122a across a tissue surface having a complex geometry while the surface of electrically conductive portion 2135 remains substantially parallel to the tissue surface. It should be understood that member 2166 and/or cavity 2164 can include stops or can be shaped differently so as to allow for more or less freedom of movement. Further, recess 2162 and cavity 2164 can be positioned in upper bumper portion 2160, for example, more proximally or distally than shown.

Extending through flexible member 2140 and through an aperture 2155 in member 2166 is a power lead 2150. A distal end portion 2152 of power lead 2150 is electrically coupled to L-shaped electrode 2130 to deliver energy to electrically conductive surface 2135. Distal end portion 2152 has sufficient slack to avoid breaking or disconnecting from electrode 2130 while bumper 2122 pivots relative to flexible portion 2140. A proximal end of power lead 2150 is coupled to an electrical energy source (not shown), as discussed above. It should be understood that power lead 2150 can be coupled to electrode 2130 without passing through flexible member 2140.

A number of embodiments have been described. Nevertheless, it will be understood that various modifications can be made. For example, the bumper can be directly or indirectly pivotably coupled to the shaft. In addition, the bumpers can have any suitable number of sides arranged in any suitable shape, such as a parallelepiped, a triangular prism or a half dome with a planar tissue contacting surface. Also, in bumper 1022, projection 1064 can be deformed by a method other than heating, such as, for example, by mechanical deformation. Moreover, upper bumper portion 1060 and lower bumper portion 1070 can be joined by another mechanism such as friction fit, press fit, or adhesive, or can be made as a single piece. Flexible portions 26, 940, and 1040 can be a nitinol wire not in a superelastic state, or can be another elastic or superelastic component, such as a stainless steel or plastic spring. Both the shaft and the nitinol wire can be resiliently flexible to provide additional flexibility. In addition, the flexing action of the flexible portion can be in a direction other than that shown. Likewise, the bumper can pivot about an axis in a different direction than the direction shown. Also, the proximal ends of flexible portions 26, 940, 1040, and 1740 can be attached to the shaft by any suitable means, such as, for example, by crimping, welding, or press-fitting. The electrodes can be made of any biocompatible electrically conductive material, such as, for example, stainless steel, tungsten, gold, silver, or platinum. The electrically conductive surface of an embodiment can, for example, be flush from the tissue contacting surface, project from the tissue contacting surface, or be recessed in the tissue contacting surface. In addition, the electrically conductive surfaces can be, for example, planar or curved. Moreover, the probe can include more than one electrically conductive surface and/or return electrode, such as, for example an array of electrically conductive surfaces on the bumper. The features described for the various embodiments are non-limiting. Further these features can be combined or interchanged with one another, as well as deleted and supplemented. Accordingly, these and other embodiments are within the scope of the following claims.

What is claimed is:

1. A method comprising:
   positioning an electrically conductive surface of a head of an instrument adjacent to a cartilage surface, the head coupled to a shaft through a flexible portion, the head offset from an axis of the shaft of the instrument by a distance D in a range of 0.01 to 0.40 inches and by an angle $\alpha$ in a range of 0 to 45 degrees on either side of the axis, the flexible portion configured to flex in at least one direction and the head configured to pivot about the axis of the shaft substantially perpendicular to that direction;
   moving the shaft relative to the cartilage surface, whereby moving the shaft relative to the cartilage surface causes the head to pivot relative to the cartilage surface; and
   applying electrical energy to the electrically conductive surface to treat chondromalacia.

2. The method of claim 1, further comprising sliding the head across the cartilage surface.

3. The method of claim 2, wherein the electrically conductive surface remains substantially in contact with the cartilage surface as the head slides across the cartilage surface.

4. The method of claim 1, further comprising biasing an electrically conductive surface of the head towards the cartilage surface using the flexible portion of the instrument.

5. The method of claim 4, wherein the head includes a substantially planar, flat non-conductive tissue contact surface and a portion enclosing a part of the flexible portion.

6. The method of claim 5, wherein the part of the flexible portion enclosed by the head defines an axis substantially transverse to a longitudinal axis of the shaft and about which the head is free to pivot.

7. The method of claim 4, wherein moving the shaft relative to the cartilage surface comprises orienting the electrically conductive surface of the head substantially parallel to the cartilage surface.

8. The method of claim 4, wherein the electrically conductive surface has at least a portion recessed in or projecting from a flat, non-conductive surface of the head.

9. The method of claim 4, wherein the electrically conductive surface has a first surface area and a non-conductive surface of the head has a second surface area, the first surface area is smaller than the second surface area.

10. The method of claim 1, wherein applying electrical energy comprises applying electrical energy via a flexible power lead coupled between the shaft and the electrically conductive surface.

11. The method of claim 1, wherein the head is offset from a longitudinal axis of a shaft.

12. The method of claim 1, wherein the electrically conductive surface is a surface of an electrode.

13. The method of claim 12, wherein the electrode is an 'L' shaped electrode.

14. The method of claim 12, wherein the electrode is a 'T' shaped electrode.

15. The method of claim 1, wherein the head includes a substantially planar, flat non-conductive tissue contact surface and a portion enclosing a part of the flexible portion.

16. The method of claim 15, wherein the electrically conductive surface is flush with the non-conductive tissue contact surface.

17. The method of claim 15, wherein the electrically conductive surface is recessed in the non-conductive tissue contact surface.

18. The method of claim 1 wherein the head is flexibly biased against the cartilage surface throughout shaft movement.

19. The method of claim 1 wherein the head is flexibly attached to the shaft for maintaining electrical conductivity throughout shaft movement.

* * * * *